United States Patent [19]

Wu et al.

[11] Patent Number: 5,115,100

[45] Date of Patent: May 19, 1992

[54] PURIFICATION OF HEMOGLOBIN AND METHEMOGLOBIN BY BIOSELECTIVE ELUTION

[75] Inventors: Xiang-Fu Wu, Shanghai, Switzerland; Jeffrey T. Wong, Don Mills, Canada

[73] Assignee: Kinetic Investments Limited, Don Mills, Canada

[21] Appl. No.: 394,945

[22] Filed: Aug. 17, 1989

[30] Foreign Application Priority Data

Aug. 17, 1988 [CA] Canada .................................. 575010

[51] Int. Cl.$^5$ ...................... A61K 35/14; C07K 13/00
[52] U.S. Cl. .................................................... 530/385
[58] Field of Search ........................... 530/385; 514/6

[56] References Cited

U.S. PATENT DOCUMENTS 4,407,961 10/1983 Sanders ................................. 436/67
4,600,531 7/1986 Walder ................................ 530/385

OTHER PUBLICATIONS

Hsia et al. (1986), Purification of Stroma-free Haemoglobin by ATP-agarose Affinity Chromatography, J. Chrom. 374:143-148.

Primary Examiner—Howard E. Schain
Assistant Examiner—Richard C. Ekstrom
Attorney, Agent, or Firm—Ridout & Maybee

[57] ABSTRACT

A method for purifying hemoglobin, mixed with other proteins is described, wherein the mixture is contacted with an ion exchange matrix so that the hemoglobin is adsorbed to it. The matrix is washed to remove unadsorbed components, and the hemoglobin is then selectively eluted using a ligand which specifically binds the hemoglobin causing it to desorb from the matrix. The method can also be used to effect reduction of methemoglobin to hemoglobin on an ion exchange matrix followed by selective elution to achieve purification. The method can also be used to purify methemoglobin.

18 Claims, 2 Drawing Sheets

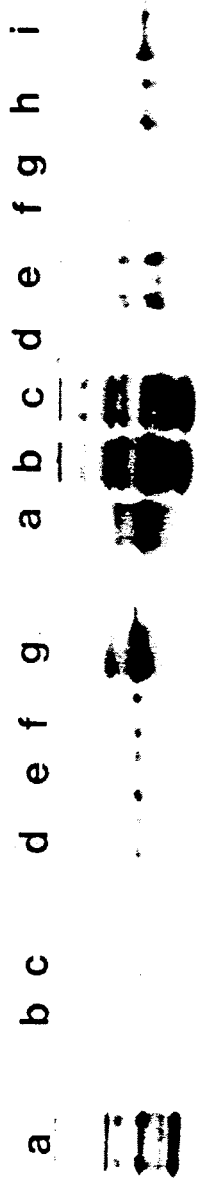
FIG. 6
FIG. 7
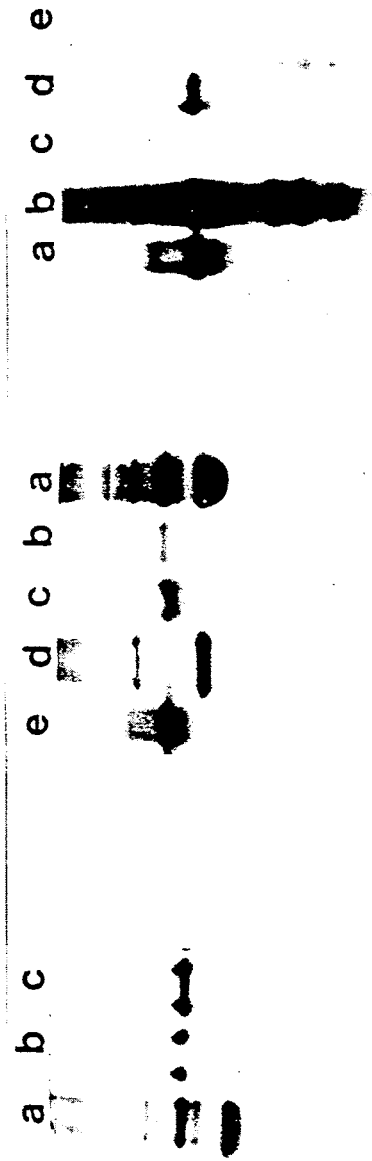
FIG. 8
FIG. 9
FIG. 10

PURIFICATION OF HEMOGLOBIN AND METHEMOGLOBIN BY BIOSELECTIVE ELUTION

This invention relates to a method for purifying hemoglobin and methemoglobin, which are collectively referred to herein as hemoproteins. The term "hemoproteins" as used herein is intended to be restricted to hemoglobin and methemoglobin. More particularly, the invention provides a method for economically separating hemoglobin from other proteins on a large scale. The method employs the techniques of bioselective elution, wherein the hemoglobin and protein mixture is adsorbed to an ion exchange matrix and hemoglobin is selectively eluted using a biospecific ligand.

It has long been desired to have a hemoglobin-based blood substitute or "synthetic blood", which would be cheaply and plentifully available. Recently, synthetic bloods of various compositions have been produced and have been shown to be suitable substitutes for whole cellular blood in a wide range of applications.

Replacement of blood is most often used to maintain the circulation volume of the blood fluid and to provide the blood volume with sufficient oxygen transport capacity to meet the requirements of cellular respiration in the organism. In maintaining circulation volume, it is essential that the fluid medium have dissolved macromolecules which will maintain the osmotic pressure of the medium. These requirements are readily met by present day blood replacement practices; however, supplies of human blood for replacement purposes is dependent on donation by healthy individuals, and there are continual problems associated with storing, processing and typing donated blood.

Synthetic blood has the advantages of being sterile, being compatible with all blood types, and having a long shelf life. If synthetic blood can be made economically, a constant supply would become available, which would not be dependent on blood donations.

The development of synthetic blood followed from the finding that stroma-free hemoglobin solutions embody many of the attributes of an ideal blood substitute; however, because of its small size, hemoglobin is too rapidly excreted through the kidneys, necessitating replenishment at short intervals. A number of approaches have been developed to slow down the excretion of hemoglobin in a synthetic blood, including crosslinking the four globin subunits of hemoglobin, polymerising the hemoglobin, conjugating the hemoglobin to a carrier molecule such as dextran or polyethyleneglycol, or encapsulating the hemoglobin within liposomes. The different types of hemoglobin-based blood substitutes so obtained are capable of delivering oxygen to tissues, and exhibit plasma halflives from several hours to two days. Their syntheses all require hemoglobin, usually human, as starting material, which is presently obtainable from outdated blood from bloodbanks.

Normal human hemoglobin is a tetramer consisting of two alpha and two beta globin chains, each chain containing a heme group. Hemoglobin is a member of a family of related hemoproteins, with methemoglobin being another significant member. Human fetal hemoglobin consists of two alpha and two gamma globin chains. The present invention is useful for purifying hemoproteins generally, but for the purpose of manufacturing synthetic blood, the inventive method is particularly important in the purification of human adult hemoglobin.

With the advent and rapid development of recombinant DNA technologies, the prospect of economically obtaining human globins from cultured microorganisms or cells has become more promising. An important limiting factor in terms of cost in the synthesis of globins by way of recombinant DNA resides in the need to separate the alpha and beta globins from host proteins, to assemble two alpha and two beta chains into a tetramer, to insert a heme molecule (most likely in the form of hemin) into each globin chain at an appropriate stage, and to reduce the hemin groups in the tetramer from the ferric to the ferrous form, i.e. from methemoglobin to hemoglobin. Methods that facilitate such downstream processing of the globins into purified, functional hemoglobin, therefore, become crucial to the economic feasibility of hemoglobin production using recombinant DNA. These methods would also be useful for obtaining purified hemoglobin from outdated blood, since unwanted proteins in addition to hemoglobin are released upon the lysis of erythrocytes.

The present invention utilizes the principles of biospecific or bioselective elution to achieve a rapid, simple purification of hemoglobin and related hemoproteins from other proteins. When exposed to air, hemoglobin readily binds oxygen, and in its oxygenated form is properly termed (oxy)hemoglobin. However, as used herein the term "hemoglobin" is intended to include hemoglobin in its oxygenated and deoxygenated forms, and it will be apparent to the skilled person which form of hemoglobin is being referred to from the context in which the term is used.

Prior to the present invention, affinity chromatography has been used to separate hemoglobin from other proteins. In 1982 K. Tsutsui and G. C. Mueller described the use of hemin-agarose to purify heme-binding proteins, including globin (Analytical Biochemistry, 121, 244–250). J. C. Hsia and S. S. Er described the use of ATP-agarose for the affinity chromatographic purification of hemoglobin (J. Chromatography, 374, 143-8 (1986); International patent applications WO87/00177 and WO87/04169). These prior known purification methods require the preparation of biospecific chromatographic matrices. For example, a ligand, such as ATP, which is biospecific to hemoglobin under anticipated chromatography conditions, is attached to an agarose matrix, and the hemoglobin-containing mixture is contacted with the matrix, the hemoglobin selectively being bound to the ATP ligand. While biospecific chromatographic matrices are useful for purifying hemoglobin on a small scale, they are very expensive due to the need to custom synthesize the specialized matrices containing a covalently bonded ligand, and hence, are not suitable for large scale commercial purifications.

The present invention utilizes inexpensive, readily available conventional anionic or cationic exchange matrices and provides a low cost means for achieving large scale purification of hemoglobin. Cost effectiveness is particularly important in relation to the manufacture of hemoglobin since, in contrast to most other synthetic proteins used for medical purposes, gram quantities of the protein, e.g. 30g, are needed to provide a clinically useful dose of a hemoglobin-based blood substitute. Thus, the present invention based on the principles of biospecific elution provides a solution to the problem of developing an economic method for purifying hemoglobin. Additionally, the invention enables the added benefit of combining hemin reduction with the purification of the protein.

The principles of bioselective elution have been known for some time (see, for example, B. M. Pogell (1962), Biochem. Biophys. Res. Commun. 7, 225; and (1966), in Methods in Enzymology (W. A. Wood, ed) 9, 9). Prior to this invention, hemoglobin purification has favoured affinity chromatography possibly on the reasoning that when dealing with a complex mixture of proteins, it is only the resolving power of affinity chromatography which holds out a reasonable prospect for achieving a clean one step purification. A standard method for purifying hemoglobin from red cell extracts involves adsorption on a DEAE (diethylaminoethyl) matrix at near neutral pH (L. C. Cheung et al (1984) Anal. Biochem., 137, 481). While this method is suitable for red cell extracts, it may result in hemoglobin with a phospholipid contaminant which has been shown to give an adverse reaction in at least some animals.

Importantly, however, this standard purification technique is not suited to the purification of hemoproteins mixed with the diverse proteins expected in the production of hemoproteins by recombinant DNA procedures.

Since bioselective elution utilizes standard ion exchange resins, a skilled person might suppose that this purification technique did not possess sufficient resolving power to provide a clean separation of hemoglobin from a protein mixture which, when the hemoglobin is made using DNA recombinant technology, would contain a plurality of diverse proteins. The present invention provides the unexpected result that hemoglobin and methemoglobin can be acceptably purified from a mixture of diverse proteins using bioselective elution on standard anionic or cationic exchange matrices. Additionally, the invention includes the method of reduction of methemoglobin to hemoglobin while adsorbed on the ion exchange matrix followed by selective elution of the resultant hemoglobin in a pure form.

Accordingly, the present invention provides a method for purifying a hemoprotein mixed with other proteins, comprising contacting the protein mixture with an ion exchange matrix so that the hemoprotein component of the mixture is adsorbed to the matrix. The matrix is then washed to remove unadsorbed components, and the hemoprotein is selectively eluted from the matrix using a ligand which specifically binds to the hemoprotein causing it to desorb from the matrix.

BRIEF DESCRIPTION OF THE DRAWINGS

FIGS. 1-10 are polyacrylamide gel electrophoresis (PAGE) chromatograms showing elution fractions as described in the examples, infra.

DESCRIPTION OF THE PREFERRED EMBODIMENTS

Figures 1, 2, 3:

Synthesis of hemoglobin using recombinant DNA methods will enable the production of the alpha and beta globin subunits by the insertion of the genes coding for these globins into the genome of a host cell. The host cell may be E.coli, a yeast, a cultured mammalian cell or some other suitable host. Methods are known for the assembly of the methemoglobin tetramer, comprising two alpha and two beta globins, with four hemin groups, but undoubtedly additional work will be required to provide optimum yields for the commercial product.

Purification of the assembled methemoglobin would involve separation from contaminating proteins derived from E.coli, yeast supernatant proteins or, in the case of mammalian cell cultures, calf serum proteins. The effectiveness of the present invention is demonstrated by the examples, infra, which also include separation of hemoglobin or methemoglobin from human serum proteins and snake venom proteins.

In biospecific elution, a protein is allowed to adsorb to an ion exchange matrix, along with other proteins of comparable electric charge configuration. A ligand that binds specifically to the target protein is then added. In binding the ligand, the protein undergoes a change in its conformation, thereby altering the strength of its interaction with the matrix. Often the specific ligand carries a net charge which would result in a change in the net charge of the protein upon binding with the ligand; also altering the strength of protein interaction with the matrix. When the conformation or net charge change or both induced by the ligand results in a weakening of the protein-matrix interactions, it leads to a specific elution of the target protein, while other proteins which do not bind the ligand remain adsorbed to the matrix. Most often, a negatively charged ligand is allowed to bind to a target protein and induce its elution from a cation exchange matrix.

Hemoglobin is known to readily bind a large number of polyanionic ligands such as polyphosphates, e.g., pyrophosphate, inositol—tri, tetra, penta or hexaphosphate, ATP, ADP, 2,3-diphosphoglycerate (DPG), etc.; polycarboxylates and polysulfates, to name a few. In the present invention, the use of polyphosphates is preferred, with pyrophosphate and phytate being most preferred. A problem faced in the development of the present method was to discover those conditions where the ligand binding to hemoglobin will result in a biospecific elution of hemoglobin from an inexpensive, commercially available ion exchange matrix. The separation conditions must not be so extreme as to denature the hemoglobin. For example, the pH range should be from 4.0 to 11.0, and preferably from 5.0 to 9.5. Using the foregoing factors, biospecific elution was initially carried out using cation exchange matrices in association with pyrophosphate and phytate (inositol-hexakisphosphate) as the ligands. As shown by the examples which follow, surprisingly clean results were obtained using phosphocellulose, sulfopropyl-SEPHADEX (trade mark, Sephadex is a cross-linked dextran polysaccharide) and carboxymethyl-SEPHADEX, all of which are standard commercially available cation exchange resins. Cation exchange resins of these types are herein generically termed phospho-, sulfo- and carboxymethylpolysaccharide matrices. Surprisingly, biospecific elution of hemoglobin using pyrophosphate or phytate as the ligand also effected separation in association with conventional anion exchange resins such as DEAE-SEPHADEX (poly[2-(diethylamino)ethyl] polyglycerylene dextran hydrochloride), which is herein generally termed diethylaminoethylpolysaccharide.

The present invention also provides a method for reduction of the hemin groups in methemoglobin from the ferric to the ferrous oxidation state in combination with the biospecific elution purification. Thus, methemoglobin is adsorbed to an ion exchange matrix and washed with a reducing agent such as sodium dithionite. The resulting hemoglobin is then selectively eluted in the usual way to give the purified substance. This method for reducing methemoglobin has the advantage of minimizing the dithionite/hemoprotein contact time so that side reactions are greatly reduced as compared with solution methods.

The invention is particularly described with reference to the following examples which are provided for illustration and not to limit the scope of the invention.

EXAMPLE 1

Phosphocellulose-pyrophosphate 0.1 ml of 6% human hemoglobin in the form of a red blood cell lysate (after centrifugation to remove cell membranes) is mixed with 0.2 ml of an extraneous protein solution and 0.3 ml of 0.2 M sodium acetate buffer, pH 6.0. The mixture is placed on a column (1 cm diameter x 6 cm height) of phosphocellulose (Whatman Co., grade P11) equilibrated with the same 0.2 M sodium acetate buffer pH 6.0. The column is developed with 3x bed volumes each of successively:
  (a) full strength 0.2 M sodium acetate buffer, pH 6.0, to wash away unadsorbed and lightly adsorbed, proteins;
  (b) 0.01 M–0.02 M sodium pyrophosphate/0.02 M sodium acetate, pH 6.0, which elutes some hemoglobin, and also some lightly adsorbed proteins;
  (c) 0.04 M sodium pyrophosphate/0.02 M sodium acetate, pH 6.0, which desorbs the hemoglobin.

FIG. 1 shows the electrophoresis results of the method of Ex. 1 starting with 0.1 ml of 6% hemoglobin and 0.2 ml of an extract of *E.coli* proteins prepared by extracting for 30 min. 0.1 g of an *E.coli* acetone powder with 2 ml of 0.2 M sodium acetate, pH 6.0, and removing insolubles by centrifugation. Lane a shows the mixture of hemoglobin and *E.coli* proteins. Lanes b and c are fractions eluted by 0.2 M sodium acetate buffer. Lane d is a fraction eluted by 0.01 M pyrophosphate. Lane e is control hemoglobin as a reference, and lane f shows purified hemoglobin eluted from the ion exchange matrix by 0.04 M pyrophosphate. Note that the reference sample of control hemoglobin contained an extra protein band compared to the purified hemoglobin in lane f. This is because the control hemoglobin was actually a red blood cell lysate, which contained other red cell proteins besides hemoglobin.

FIG. 2 shows the electrophoresis results of the method of Ex. 1 starting with 0.1 ml 6% hemoglobin and 0.2 ml of the macromolecules from draft beer which would contain proteins from the supernatant of cultivated yeast cells. The freeze-dried powder of dialysed draft beer was dissolved in water at a concentration of 200 mg/ml. Lane a shows the mixture of beer proteins and hemoglobin. Lane b shows the fraction eluted by 0.2 M sodium acetate buffer. Lane c shows the fraction eluted by 0.01 M pyrophosphate. Lane d shows purified hemoglobin eluted by 0.04 M pyrophosphate as compared to reference hemoglobin in lane e.

FIG. 3 shows the electrophoresis results of the method of Ex. 1 on red blood cell lysate. Lane a shows the red blood cell lysate. Lane b shows the fraction on elution with 0.01 M pyrophosphate; lane c elution with 0.02 M pyrophosphate; and lane d shows purified hemoglobin on elution with 0.04 M pyrophosphate.

Figures 4, 5:

FIG. 4 shows the electrophoresis results of the method of Ex. 1 starting with 0.1 ml 6% hemoglobin and 0.2 ml snake venom solution prepared by dissolving dried Agkistrodon halys venom in water at 100 mg/ml. Lane a is reference hemoglobin. Lane b shows the sample mixture. Lane c is the fraction eluted by 0.2 M sodium acetate buffer. Lane d is the fraction eluted by 0.01 M pyrophosphate, and lane e shows purified hemoglobin eluted by 0.04 M pyrophosphate.

EXAMPLE 2

Sulfopropyl-Sephadex-Pyrophosphate

Although phosphocellulose works well in Example 1, other cation-exchanging matrices also provide useful purification by means of biospecific elution, including sulfopropyl-Sephadex (SP-Sephadex).

0.1 ml of 6% hemoglobin is mixed with 0.2 ml of calf serum (from Gibco Laboratories) and 0.3 ml of 0.2 M sodium acetate buffer, pH 6.0. The mixture is placed on a 1 cm x 6 cm column of sulfopropyl-Sephadex (SP-Sephadex), equilibrated with the same 0.2 M sodium acetate pH 6.0 buffer. The column is then successively developed with three bed volumes of each of:
  (a) 0.2 M sodium acetate buffer, pH 6.0
  (b) 0.01 M sodium pyrophosphate/0.02 M sodium acetate, pH 6.0.

FIG. 5 shows the electrophoresis of this example, wherein lane a shows the starting mixture of calf serum and hemoglobin. Lanes f and g show the fractions eluted by 0.2 M sodium acetate buffer, and lanes h and i show purified hemoglobin eluted by 0.01 M pyrophosphate.

EXAMPLE 3

Carboxymethyl-Sephadex-Pyrophosphate

Like Sulfopropyl-Sephadex, carboxymethyl-Sephadex (CM-Sephadex) is also a useful cation exchanger.

0.1 ml 6% hemoglobin solution is mixed with 0.2 ml calf serum and 0.3 ml of 0.2 M sodium acetate buffer, pH 6.0, and placed on a 1 cm x 6 cm column of C-50 grade CM-Sephadex. The column is then developed with three bed volumes each of, successively:
  (a) 0.2 M sodium acetate buffer, pH 6.0
  (b) 0.01 M sodium pyrophosphate/0.02 M sodium acetate, pH 6.0
  (c) 0.04 M sodium pyrophosphate/0.02 M sodium acetate, pH 6.0.

FIG. 5 also shows the electrophoresis of this example, wherein lanes b and c show the fractions eluted by 0.01 M pyrophosphate, and lanes d and e show purified hemoglobin eluted by 0.04 M pyrophosphate.

EXAMPLE 4

Phosphocellulose-Pyrophosphate Batch Process

In Example 1, the biospecific elution is performed on a column of the cation exchanger phosphocellulose. In this example, it is demonstrated that biospecific elution may be performed in a batch process instead of a column process.

A suspension of phosphocellulose P11 was prepared by dispersing 4.5 ml of packed gel in 5.5 ml of 0.2 M sodium acetate buffer, pH 6.0. 0.1 ml of 6% hemoglobin and 0.2 ml of calf serum were added to the suspension, which was stirred at room temperature for 30 minutes. Afterwards, the gel was placed on suction filtration to remove excess fluid. It was washed (a) first with 0.2 M sodium acetate, pH 6.0, then (b) 0.01 M pyrophosphate in 0.02 M sodium acetate, pH 6.0, and (c) 0.04 M pyrophosphate in 0.02 M sodium acetate, pH 6.0. The washing steps (a) and (b) and the elution step (c) were each performed with 3×15 ml of solution.

FIG. 6 shows the electrophoresis of this example, wherein lane a shows the starting mixture. Lanes b and c show the fractions eluted with 0.01 M pyrophosphate, and lanes d, e and f show purified hemoglobin upon elution with 0.04 M pyrophosphate. Lane g is reference hemoglobin.

EXAMPLE 5

Phosphocellulose-Phytate

In the preceding Examples, pyrophosphate is employed as the affinity ligand to bring about a specific elution of hemoglobin from a cation exchange matrix. This example shows the feasibility of using other affinity ligands as well: in this instance inositol-hexakisphosphate, or phytate.

0.1 ml of 6% hemoglobin is mixed with 0.2 ml calf serum and 0.3 ml of 0.2 M sodium acetate buffer pH 5.0, and placed on a 1 cm×6 cm column of phosphocellulose (Sigma Co.). The column is treated successively with three bed volumes each of:
(a) 0.2 M sodium acetate buffer, pH 5.0
(b) 0.005 M sodium phytate in 0.02 M sodium acetate buffer, pH 5.0
(c) 0.01 M sodium phytate in 0.02 M sodium acetate buffer, pH 5.0.

FIG. 7 shows the electrophoresis of this example, wherein lane a is reference hemoglobin, and lane b is the sample mixture. Step (a) is shown in lanes c and d, and step (b) in lanes e, f and g. It can be seen that some hemoglobin is eluted with 0.005 M phytate. Lanes h and i show purified hemoglobin resulting from step (c).

It should be noted that this particular grade of phosphocellulose required the use of pH 5 buffer. It will be understood by those skilled in the art that suitable adjustments to process conditions may be called for to different manufacturers or from different batches from a common manufacturer.

EXAMPLE 6

Phosphocellulose—Pyrophosphate Dithionite Reduction

When heme is inserted into alpha and beta globin chains, it is in the form of ferric heme or hemin, on account of the instability of ferrous heme when it is detached from globins. Consequently, in assembling mature hemoglobin from alpha and beta globins, at some stage the heme inserted into the globins must undergo reduction. In this example, the affinity elution method of hemoglobin purification is shown to be feasible starting with methemoglobin (containing hemin) derived from globin chains and hemin, rather than hemoglobin (containing ferrous heme) as in the preceding Examples. Moreover, the reduction of hemin to heme by means of a reducing agent such as dithionite can be performed conveniently within the purification sequence, thereby permitting a combination of the purification and reduction steps, which simplify the operation and reduce costs.

2 ml of a 2% globin solution (prepared from hemoglobin, containing both alpha and beta chains) in 0.01 M phosphate buffer, pH 7.4 was stirred at room temperature. A hemin solution is prepared by dissolving 3 mg hemin (Sigma Chemical Co.) in a minimal volume of 0.1 N NaOH and diluted with distilled water to 2.5 ml. 0.2 ml of this hemin solution was added to the stirred globin solution. After 10 minutes, the mixture was filtered through filter paper to remove insoluble material.

0.3 ml of the reconstituted methemoglobin obtained in the filtrate, 0.3 ml human serum, and 0.6 ml 0.2 M sodium acetate buffer, pH 6.0, were added to a phosphocellulose P11 column (1 cm×5 cm), equilibrated with the same buffer. Eight ml of 0.01 M sodium dithionite in 0.02 M sodium acetate buffer, pH 6.0, was passed through the column in order to reduce the methemoglobin adsorbed to the phosphocellulose. Afterwards, the column was treated with, successively, three bed volumes of each of:
(a) 0.2 M sodium acetate buffer, pH 6.0
(b) 0.01 M pyrophosphate in 0.02 M sodium acetate buffer, pH 6.0
(c) 0.04 M pyrophosphate in 0.02 M sodium acetate buffer, pH 6.0.

FIG. 8 shows the electrophoresis of this example, wherein lane a is the sample mixture. Lane b shows the fraction eluted by 0.01 M pyrophosphate, and lane c shows elution by 0.04 M pyrophosphate, both lanes exhibiting purification of hemoglobin. In this Example, excess globins were employed relative to the amounts of hemin added, showing that exact stochiometric ratios between globins and hemin were unnecessary for the method to be effective. Exact stochiometric ratios are expected to be difficult to obtain when the method is to be applied to globins prepared by gene cloning methodology.

The following examples show the method of the invention used in association with an anion exchange matrix.

EXAMPLE 7

DEAE—Sephadex-Phytate 0.1 ml of 6% hemoglobin is mixed with 0.2 ml human serum and 0.3 ml of 0.2 M Tris-HCl buffer pH 9.4, and placed on a column (1 cm diameter×5 cm height) of DEAE Sephadex A-50 anion exchanger which has been equilibrated with the same 0.2 M Tris-HCl pH 9.4 buffer. The column is treated successively with four bed volumes each of:
(a) 0.2 M Tris-HCl, pH 9.4
(b) 0.003 M phytate and 0.02 M Tris-HCl, pH 9.4
(c) 0.05 M phytate and 0.02 M Tris-HCl, pH 9.4
(d) 0.10 M sodium acetate buffer, pH 6.0, containing 0.5 M NaCl.

FIG. 9 shows the electrophoresis of this example, wherein lane a is the sample mixture. Lane b shows hemoglobin eluted by 0.003 M phytate and 0.02 M Tris-HCl, and lane c shows hemoglobin eluted by 0.05 M phytate/0.02 M Tris-HCl. Lane d shows other proteins eluted by 0.1 M sodium acetate/0.5 M NaCl, and lane e shows reference hemoglobin.

EXAMPLE 8

DEAE—Sephadex-Pyrophosphate 0.1 ml of 6% hemoglobin is mixed with 0.2 ml of snake venom (100 mg/ml Agkistrodon halys venom) and 0.3 ml 0.2 M Tris-HCl buffer, pH 9.4, and loaded on a DEAE Sephadex A-50 column (1 cm×5 cm). The column is treated successively with:
(a) 0.2 M Tris-HCl buffer, pH 9.4 (3 volumes)
(b) 0.005 M pyrophosphate and 0.02 M Tris-HCl, pH 9.4 (4 volumes)
(c) 0.1 M sodium acetate buffer, pH 6.0, containing 0.5 M NaCl (3 volumes).

FIG. 10 shows the electrophoresis of this example, wherein lane a is reference hemoglobin, and lane b is the sample mixture. Lane c shows the proteins eluted by 0.2 M Tris-HCl. Lane d shows hemoglobin eluted by 0.005 M pyrophosphate/0.02 M Tris-HCl, and lane e shows proteins eluted by 0.1 M sodium acetate/0.5 M NaCl.

We claim:

1. A method for purifying a hemoprotein mixed with other non-hemoproteins, comprising:
    contacting the protein with an ion exchange matrix selected from the group consisting of phosphopolysaccharide, sulfopolysacharide, carboxymethylpolysaccharide and diethylaminoethylpolysaccharide, so that at least the hemoprotein component of the mixture is absorbed to the matrix along with some of the other non-hemoproteins;
    washing the matrix to remove unadsorbed components; and
    selectively eluting the hemoprotein using a ligand which specifically binds to the hemoprotein causing it to desorb from the matrix leaving the non-hemoprotein adsorbed to the matrix.

2. A method as claimed in claim 1, wherein the hemoprotein is hemoglobin.

3. A method as claimed in claim 1, wherein the hemoprotein is methemoglobin.

4. A method as claimed in claim 1, wherein the pH is controlled by the use of buffers.

5. A method as claimed in claim 1, wherein the method is conducted in a pH range of from 4.0 to 11.0 so that the hemoglobin is not denatured.

6. A method as claimed in claim 5, wherein the method is conducted in a pH range of from 5.0 to 9.5.

7. A method as claimed in claim 1, wherein the ligand is a polyanion.

8. A method as claimed in claim 7, wherein the ligand is a polyanion selected from the group: phosphates, carboxylates, and sulfates.

9. A method as claimed in claim 8, wherein the ligand is pyrophosphate.

10. A method as claimed in claim 8, wherein the ligand is phytate.

11. A method for reducing methemoglobin and separating the resulting hemoglobin from a mixture of proteins including non-hemoproteins, comprising:
    contacting the protein mixture containing methemoglobin with an ion exchange matrix selected from the group consisting of phosphopolysaccharide, sulfopolysaccharide, carboxymethylpolysaccharide and diethylaminoethylpolysaccharide so that at least the methemoglobin is adsorbed to the matrix along with some of the other non-hemoproteins;
    contacting the methemoglobin-containing matrix with a reducing agent so that the methemoglobin is reduced to the hemoglobin;
    washing the matrix to remove unadsorbed components; and
    selectively eluting the hemoglobin using a ligand which specifically binds to the hemoglobin causing it to desorb from the matrix leaving the non-hemoproteins adsorbed to the matrix.

12. A method as claimed in claim 11, wherein the pH is controlled by the use of buffers.

13. A method as claimed in claim 11, wherein the method is conducted in a pH range of from 4.0 to 11.0 so that the hemoglobin is not denatured.

14. A method as claimed in claim 13, wherein the method is conducted in a pH range of from 5.0 to 9.5.

15. A method as claimed in claim 11, wherein the ligand is a polyanion.

16. A method as claimed in claim 15, wherein the ligand is a polyanion selected from the group: phosphates, carboxylates, and sulfates.

17. A method as claimed in claim 16, wherein the ligand is pyrophosphate.

18. A method as claimed in claim 16, wherein the ligand is phytate.

* * * * *